United States Patent
Thomas et al.

(10) Patent No.: US 12,251,488 B2
(45) Date of Patent: Mar. 18, 2025

(54) STERILE CONTAINER UNIT HAVING AN INFORMATION CARRIER WHICH CAN BE RIGIDLY FIXED BY MEANS OF A CLOSURE ELEMENT

(71) Applicant: Aesculap AG, Tuttlingen (DE)

(72) Inventors: Stefan Thomas, Tuttlingen (DE); Frank Weller, Markkleeberg (DE)

(73) Assignee: Aesculap AG, Tuttlingen (DE)

( * ) Notice: Subject to any disclaimer, the term of this patent is extended or adjusted under 35 U.S.C. 154(b) by 965 days.

(21) Appl. No.: 17/258,216

(22) PCT Filed: Jul. 11, 2019

(86) PCT No.: PCT/EP2019/068707
§ 371 (c)(1),
(2) Date: Jan. 6, 2021

(87) PCT Pub. No.: WO2020/011933
PCT Pub. Date: Jan. 16, 2020

(65) Prior Publication Data
US 2021/0268137 A1    Sep. 2, 2021

(30) Foreign Application Priority Data
Jul. 13, 2018   (DE) ...................... 10 2018 117 045.9

(51) Int. Cl.
*A61L 2/26*   (2006.01)
*B65D 25/20*  (2006.01)
*B65D 43/02*  (2006.01)

(52) U.S. Cl.
CPC .............. *A61L 2/26* (2013.01); *B65D 25/205* (2013.01); *B65D 43/0212* (2013.01); *A61L 2202/182* (2013.01); *A61L 2202/24* (2013.01)

(58) Field of Classification Search
CPC .. B65D 25/205; B65D 25/28; B65D 43/0225; B65D 43/0227; B65D 43/0235; A61L 2/26
(Continued)

(56) References Cited

U.S. PATENT DOCUMENTS 4,915,913 A * 4/1990 Williams ............... B65D 45/24
                                                          436/1
5,205,413 A * 4/1993 Cautereels ............... A45C 5/00
                                                         206/541
(Continued)

FOREIGN PATENT DOCUMENTS

CN    105658383 A    6/2016
CN    107206116 A    9/2017
(Continued)

OTHER PUBLICATIONS

Written Opinion received in Application No. PCT/EP2019/068707 dated Nov. 13, 2019, 14 pages.
(Continued)

*Primary Examiner* — Anthony D Stashick
*Assistant Examiner* — Raven Collins
(74) *Attorney, Agent, or Firm* — Christopher A. Rothe; CM Law

(57) ABSTRACT

A sterile container unit for receiving items which are sterilized or are to be sterilized includes a container tray and a container lid that can be coupled to the container tray by a closure element. The closure element can be actuated by a pivoting movement. An information carrier can be interlockingly fastened to the container tray and set up to display information regarding the content of the sterile container unit. The container tray, the closure element and the information carrier are adapted to one another such that, following the pivoting movement of the closure element, the
(Continued)

information carrier is rigidly fixed/locked on the container tray.

12 Claims, 5 Drawing Sheets

(58) Field of Classification Search
USPC .................................................. 206/459.5
See application file for complete search history.

(56) References Cited

U.S. PATENT DOCUMENTS

| | | | |
|---|---|---|---|
| 5,372,787 | A | 12/1994 | Ritter |
| 6,247,609 | B1 | 6/2001 | Gabele et al. |
| 10,427,841 | B2 | 10/2019 | Weisshaupt et al. |
| 2003/0080571 | A1* | 5/2003 | Schainholz ............... A61L 2/28 292/310 |
| 2004/0256270 | A1 | 12/2004 | Gleichauf et al. |
| 2006/0162210 | A1 | 7/2006 | Bauer |
| 2016/0213115 | A1 | 7/2016 | Gonitianer et al. |
| 2017/0360976 | A1 | 12/2017 | Thomas et al. |
| 2019/0298472 | A1 | 10/2019 | Schuster et al. |
| 2019/0358357 | A1* | 11/2019 | Bohnenstengel ......... A61L 2/26 |

FOREIGN PATENT DOCUMENTS

| | | |
|---|---|---|
| DE | 3316141 A1 | 11/1984 |
| DE | 9212315 U1 | 11/1992 |
| DE | 19851239 A1 | 5/2000 |
| DE | 202011052081 U1 | 2/2012 |
| DE | 102012215121 A1 | 5/2014 |
| DE | 2016118083 A1 | 3/2018 |
| DE | 102016123864 A1 | 6/2018 |
| EP | 0588228 A1 | 3/1994 |
| EP | 0882458 A2 | 12/1998 |
| EP | 2179746 A1 | 4/2010 |
| GB | 879657 A | 10/1961 |
| WO | 2004018305 A2 | 3/2004 |
| WO | 2015039868 A1 | 3/2015 |
| WO | 2018104390 A1 | 6/2018 |

OTHER PUBLICATIONS

German Search Report received in Application No. 102018117045.9 dated Jan. 16, 2017, 13 pages.
International Search Report received in Application No. PCT/EP2019/068707, dated Nov. 13, 2019, 6 pages.
Office Action received in Chinese Application No. 201980046263.7 dated Aug. 1, 2022, with translation, 24 pages.

* cited by examiner

STERILE CONTAINER UNIT HAVING AN INFORMATION CARRIER WHICH CAN BE RIGIDLY FIXED BY MEANS OF A CLOSURE ELEMENT

CROSS-REFERENCE TO RELATED APPLICATIONS

This application is the United States national phase entry of International Application No. PCT/EP2019/068707, filed Jul. 11, 2019, which claims the benefit of priority of German Application No. 10 2018 117 045.9, filed Jul. 13, 2018. The contents of International Application No. PCT/EP2019/068707 and German Application No. 10 2018 117 045.9 are incorporated by reference herein in their entireties.

FIELD

The present invention relates to a sterile container unit used in hospitals, clinics, laboratories or similar facilities, for example, to transport sterilized items or items to be sterilized, such as medical, in particular surgical, tools/utensils.

BACKGROUND

The sterile container unit represents a sterile barrier to the environment for the container content, which prevents contamination of the transported items. As soon as a container lid of the sterile container unit is opened, the sterile barrier is no longer in place, so that opening it is followed either by renewed sterilization or immediate use of the transported items. In order to inform an operator/viewer about the contents of the sterile container unit in the closed state, information carriers are attached to the outside of the container unit.

During the transport of sterile container units, they are exposed to external factors such as impacts, vibrations and drafts. These can cause the information carrier to become detached from the rest of the sterile container unit, making it impossible to tell from the outside what contents the container unit is filled with. This makes it necessary to open the container unit, which contaminates the contents and requires further sterile processing in a sterilizer/autoclave. This results in additional costs (processing, transport) as well as loss of time (surgery postponements), which reduce the economic efficiency and logistics in the respective hospitals, clinics, laboratories or similar facilities.

In order to prevent the information carriers from becoming detached, they can be attached to the container unit by gluing, riveting, welding or similar methods. Although robust holding of the information carriers is thus realized, they are very difficult to decouple from the sterile container unit, usually only in a destructive way.

Furthermore, it is possible to place the information carrier, for example in the form of a label or an RFID tag, in a receiving device, such as a slide-in unit or a clamp, integrally attached to the sterile container unit, as is known from, e.g., DE 10 2012 215 121 A1. This has either the disadvantage that the information carrier is easily detachable or, if this is not the case, that it can only be coupled to the container unit with great difficulty.

The attachment of an external information carrier in the form of a luggage label is also a solution known from the prior art. However, this is not able to guarantee a long service life, as they do not have permanent stability due to their elasticity.

In order to avoid the problem of the information carrier becoming detached, direct labeling of the sterile container unit is also conceivable. This has the disadvantage that a sterile container unit can only be used for one batch of items due to the permanent nature of the labeling, which drastically reduces its flexibility.

Ultimately, DE 10 2016 123 864 A1 discloses an information carrier that can be form-fittingly coupled with a container tray. However, this document does not contain any statement on how the information carrier can be reliably attached to the container tray or the entire remaining container unit in the transport state.

SUMMARY

In view of this prior art, the present invention is based on the object to remove or at least reduce the disadvantages of the prior art, and in particular to provide such a sterile container unit which on the one hand enables a secure, robust and permanent fixation of the information carrier, and on the other hand makes the information carrier reversibly detachable from the rest of the sterile container unit in order to provide a container tray in different states with different information on the information carrier during its lifetime.

Accordingly, the subject matter of the invention is a sterile container unit for receiving sterilized items or items to be sterilized. This consists of a container tray, a container lid which can be coupled with the container tray in a sterile sealing manner or closes the container tray in a sealing manner via a closure element which can be actuated by means of a pivoting movement, and an information carrier which can be fastened/attached to the container tray, preferably in a form-fit manner, which can also be described as an attachment component or front panel and which is prepared to receive/carry and display information about the contents of the sterile container unit. The information carrier therefore has a surface that allows, for example, a label to be efficiently attached and detached or is suitable for direct marking. The label could be designed either as a permanent label or as a disposable label. Alternatively, the information carrier can also have a clip attached, in which a label can be (temporarily) clamped.

According to the invention, the container tray, the closure element and the information carrier are matched to each other in such a way that the information carrier is rigidly fixed/locked to the container tray after/together with the pivoting movement for sealingly closing the closure element, at least in the state of the pivoted closure element.

In other words, the invention can be structurally described in such a way that a flattening of the container lid protrudes/projects beyond a side surface of the container tray extending transversely thereto, wherein the information carrier is at least partially complementary to the side wall, and that an at least partially clamp-like closure element can be tensioned/clamped/clipped onto the flattening and its protrusion beyond the side surface in such a way that the information carrier is rigidly held on the side wall by the closure element. Thus, the closure element is designed at least in sections in the manner of a pretensioned table clamp/tablecloth clamp in order to guarantee a stable fit/blocking/fixing of the information carrier to the container tray.

More specifically, the closure element relates to a claw (bracket) that is slidably held on the top/outer side, protrudes over an outer edge of the container lid and can be manually shifted towards and away from the outer edge. At least in the area of the claw as well as on the tray circumference of the container tray facing the container lid, the container tray furthermore forms a kind of collar or edge, which, when the claw is moved towards the outer edge, is gripped underneath by the claw, thereby pulling the container lid against the tray circumference in order to close the container interior in a sealing manner. The information carrier is, as already mentioned above, placed/held/locked/pressed-in/etc. (loosely/in a not yet fixed position) on the side surface of the container tray in the effective area of the claw and is secured/pressed against the side surface of the container wall by the claw when moving towards the outer edge (fixed position). It should be noted that the claw mechanism described above can also be replaced, for example, by a locking bracket, sliding or swivel latch, catch or a similar closure element, if the closure element is adapted to also secure the (initially loosely held) information carrier on the side surface of the container wall when it is moved from a non-locking position to a locking position.

This design allows to prevent unwanted loosening of the information carrier during the transport process of the sterile container unit and at the same time ensures easy, uncomplicated attachment and removal of the information carrier in various situations of use (loading of the container with attachment of the information on the contents, removal of the information during cleaning or separation of the contents, etc.). The information presented by the information carrier, which is readable by an operator, can therefore be easily changed depending on changing container contents without having to transfer/move the entire container unit into a marking position. In this way, the opposing effects of easy detachability/reversibility and reliable holding are combined in a targeted manner.

The term 'rigid' is used in the context of the invention to describe a fixation which does not allow any relative movement of the fixed components to each other. Therefore, the synonym 'immovable' or 'fixed' could be used as a synonym. 'Rigid' in no way indicates whether the state is temporary or permanent. When observing the overall teaching, a person skilled in the art can immediately understand that the fixing of the closure element to the container tray is of a temporary nature.

According to a preferred embodiment of the invention, the closure element forms at least one locking latch protrusion, which is prepared to clamp into an engagement pocket formed by the information carrier after the pivoting movement closing the container unit. This enables the closure element to engage/penetrate/sink into a designated opening in the form of the engagement pocket, which further serves a defined contact position and a resulting robust support. Further preferably, the closure element forms two or more such locking latch protrusions, which strengthens/potentiates their retention accordingly. In order to prevent the closure element from pivoting/tilting, the number of locking latch protrusions is distributed as far apart as possible on the closure element.

In this embodiment, the at least one locking latch protrusion further advantageously has a curved/bent tongue shape by forming a defined attachment point, whereby the tongue shape or attachment point in contact with the engagement pocket on the information carrier side causes such a pretension of the locking latch protrusion that it clamps the information carrier in a force-fitting manner. In this way, a force-fit closure is realized between the closure element and the information carrier, which is supported by the interaction of a (safety) form closure of the engagement pocket with the tongue shape. This form closure or at least the immersion of the locking latch protrusion into the engagement pocket also realizes a poka-yoke principle in the fixing of the closure element, since it can only be correctly locked to the container tray when the engagement pockets are engaged.

In another advantageous embodiment, the container tray forms a side surface from which a container collar protrudes in such a way that it forms a contact edge/shoulder for the information carrier, which is at least in sections complementary to the side surface. In this way, the position of the information carrier in the height direction of the container tray is defined, which further facilitates the uncomplicated assembly of the sterile container unit.

In addition to the container collar, the information carrier preferably also forms a contact shoulder, which is then prepared to be at least in sections in a flat/planar contact with the container collar. The flat contact prevents tilting/wedging of the information carrier towards the container tray and also provides a corresponding click when both surfaces touch, so that the operator is informed about the correct position of both components to each other. The flat design, at least in sections, also includes a nubbed surface where only the nubs are in contact with the container collar.

Preferably, the closure element has a clamp portion, which is prepared to at least partially grip around or under the container collar and the container lid while clamping the information carrier. The functional principle of this gripping is similar to that of a table clip/tablecloth clip and thus generates a force between the container lid and the tray that is directed towards each other, which at least supports the sterile barrier they create.

As soon as the side surface of the container tray at its respective transitions to adjacent side surfaces of the container tray, which preferably form a rectangular basic shape, has a bay window-like corner bulge in which at least one hollow-shaped container notch or slot is formed, which in turn is prepared for the form-fitting reception of an information carrier projection, the position of the information carrier relative to the container tray is fixed not only by the advantageous surface contact between contact shoulder and container collar in the height direction, but also in the side direction by the fixation between the container notch and the information carrier projection. This strengthens the position definition of the information carrier in relation to the container tray and thus simplifies their coupling. Further preferably, in each corner bulge in contact with the information carrier, i.e. in two corner bulges, two respective container notches are formed in the form of a hollow/indentation/pit.

In another advantageous embodiment, a reversible release of the information carrier from the container tray is possible after a reverse pivoting movement of the closure element, which is opposite to the closing pivoting movement. Thus, pivoting of the closure element in one direction causes rigid coupling between the information carrier and the container tray and pivoting of the closure element in another direction releases this rigid coupling again. This intuitive operating concept facilitates the handling of the sterile container unit according to the invention.

Preferably, the container lid forms a primary seal and a separate secondary seal, each of which is prepared for placement on the container tray and thus reliably creates a sterile barrier between the sterile container unit and the environment. The primary as well as the secondary seal preferably run transversely, substantially perpendicular to the surface of the container tray to which they are attached, thus realizing efficient sealing.

The closure element fixing the container lid and the information carrier further preferably has a locking lever (separate from the clamp portion), whose pivoting couples the information carrier rigidly with the container tray and the container lid. Thus, two functions are realized by this one closure element: the clamp portion clamps the container lid rigidly to the container tray with the information carrier interposed, while the locking lever ensures a fixed placement of the closure element. A seal is preferably placed around the closure element after sterilization so that it is immediately visible from the outside whether the sterile container unit has already been opened, thus preventing unauthorized removal.

BRIEF DESCRIPTION OF THE DRAWING FIGURES

The invention is explained in more detail below using preferred configuration examples with reference to the accompanying figures. The figures are merely schematic in nature and serve exclusively for understanding the invention. The same elements are marked with the same reference signs. The figures are summarized as follows.

DETAILED DESCRIPTION

Figure 1:
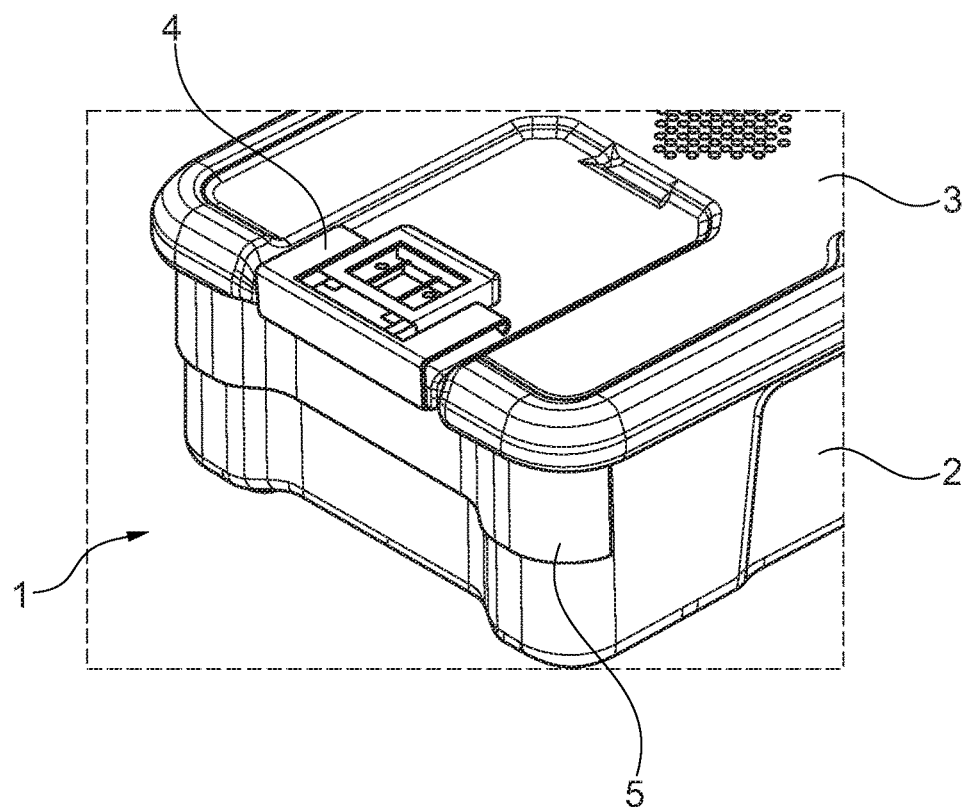
FIG. 1 is a partial perspective view of a closed sterile container unit in which a container lid and an information carrier are rigidly coupled to a container tray by a closure element.

FIG. 1 shows a sterile container unit 1 for holding sterilized utensils or utensils to be sterilized. It consists of a container tray 2, a container lid 3, a closure element 4, and an information carrier 5. The container lid 3 can be placed on the container tray 2 in a sterile sealing manner. In order to fix the connection between the container lid 3 and the container tray 2, the closure element 4 is additionally arranged. In order to make it visible from the outside which utensils are located in the (non-transparent) container tray 2, the information carrier 5 is required. The closure element 4 is optionally designed as a separate component or integrally with the container lid 3.

According to the invention, the information carrier 5 is attached to/in close contact with the container tray 2 in such a way that the closure element 4 simultaneously fixes the information carrier when actuated to fix/lock the container lid 3 to the container tray 2.

Figure 2:
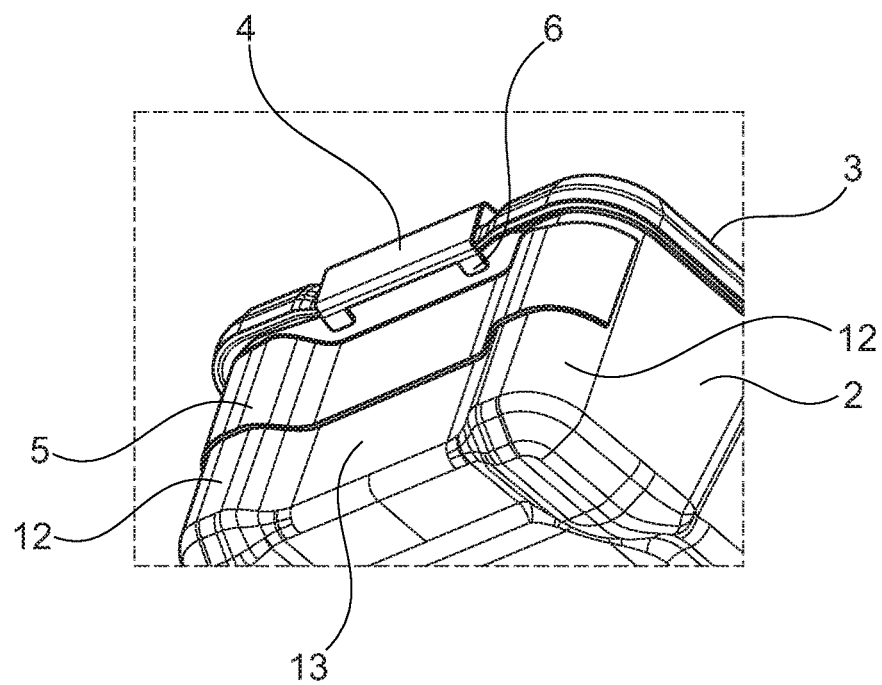
FIG. 2 is a partial perspective view that shows the sterile container unit of FIG. 1 in a view from below.

This functional principle is illustrated in FIG. 2 with reference to a preferred configuration example. The closure element 4 encompasses/encloses a projection between the container lid 3 and the container tray 2 in such a way that the information carrier 5, which is formed complementary to a side wall of the container tray 2, is clamped in place. The side wall of the container tray 2 consists of two corner bulges 12 and a container front portion 13 arranged between them. While the corner bulges 12 protrude spherically/convexly outwards/away from the sterile container interior, the container front portion is offset inwards. The information carrier 5 is designed to match this shape, so that an at least sectionally flat contact is realized between the information carrier 5 and the corner bulges 12 as well as between the information carrier 5 and the container front portion 13.

The clamping between the container lid 3 and the container tray 2, which is caused by the encompassing of the closure element 4, is positively influenced by the fact that the closure element 4 forms two flap-like and/or tongue-like locking latch protrusions 6. These locking latch protrusions 6 run essentially in a direction transverse to the container front portion 13.

Figure 3:
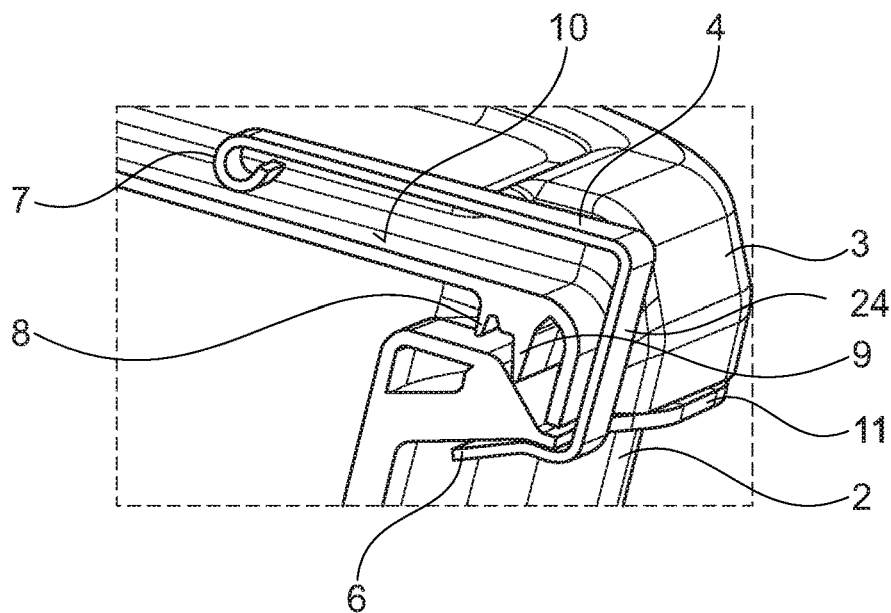
FIG. 3 is a partial perspective sectional view through the sterile container unit, in which the closure element fixes the container lid to the container tray.

For detailed descriptions of the clamping, it is referred to FIG. 3. FIG. 3 shows a perspective sectional view through the closed sterile container unit 1 along its sagittal plane. The container lid 3 has a flattening 10, which represents an indentation compared to the remaining outer surface of the container lid 3. This flattening 10 is prepared so that a clamp portion 24 of the closure element 4, which is designed like a table clamp, has an attachment point/attachment surface on the container lid via a clamping lug 7. The clamping lug 7 of the clamp portion 24 ensures a robust hold of the closure element 4 on the container lid 3.

In order to cause the clamping, the locking latch protrusions 6, one of which is shown as cut in the sectional drawing in FIG. 3, are arranged as follows. The locking latch protrusion 6 is engaged behind a container collar 11, which is integrally formed by the container tray 2. The clamp portion 24 of the closure element 4 is manufactured in such a way that there is a pretension between the locking latch protrusion 6 and the clamping lug 7 so that the clamp portion 24 counteracts a force that moves the locking latch protrusion 6 and the clamping lug 7 away from each other due to that tension. The container collar 11 is positioned transversely, preferably vertically, on the container front portion 13, which allows efficient engagement from behind by the closure element 4. The information carrier 5 is not shown in FIG. 3 for reasons of clarity.

In addition, the container lid 3 forms a primary seal 8 and a secondary seal 9, which are each prepared to be in contact with the container tray 2 and which provide a reliable sterile barrier of the sterile container unit 1 to the environment due to the serial two-stage sealing caused by them.

Figure 4:
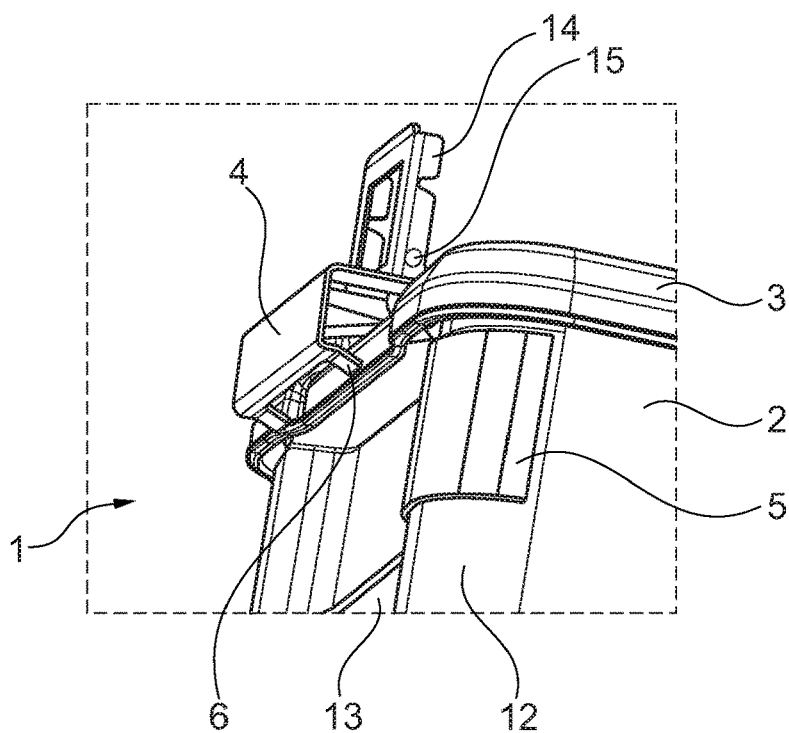
FIG. 4 is a partial perspective view that shows a state before the closure element fixes the container lid and the information carrier to the container tray.

In FIG. 4, the sterile container unit 1 is shown in a state in which the closure element 4 is open, i.e. it has not yet been pivoted for closure. This locking pivoting has to be caused by actuating a locking lever 14. The locking lever 14 and the clamp portion 24 together form the locking element 4. While the clamp portion 24 is responsible for the fixation of the information carrier 5 and the container lid 3 to the container tray 2, the locking lever 14 allows a comfortable pivoting movement around a pivot axis 15 for closing as well as for opening.

Figure 5:
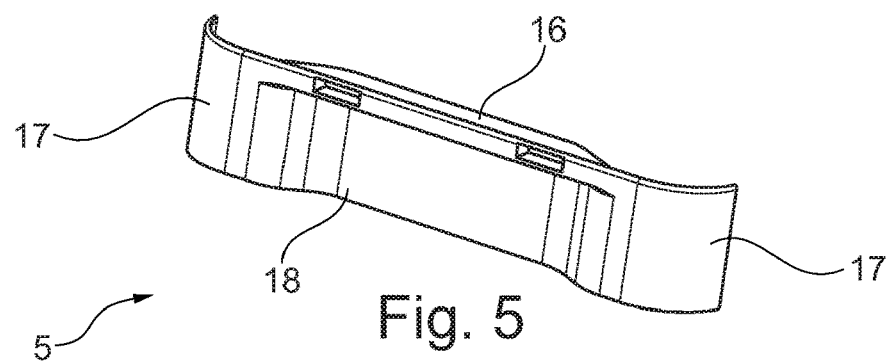
FIG. 5 is a perspective view of the information carrier from a front side.

In FIG. 5, the information carrier 5 is shown in a perspective view from a first direction. It forms a contact shoulder 16, which is prepared to establish a flat contact with the container collar 11. The contact shoulder 16 runs essentially orthogonally to an information carrier front portion 18 of the information carrier 5, which is prepared to lie flat against the container front portion 13 of the container tray. At the two lateral ends of the information carrier 5, a respective arm portion 17 is formed adjacent to the information carrier front portion 18. This in turn is prepared to lie flat against the respective corner bulge 12.

Figure 6:
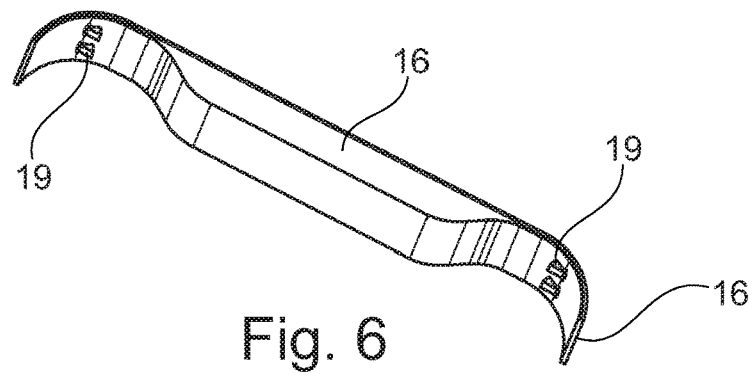
FIG. 6 is a perspective view of the information carrier from the back.

FIG. 6 shows the information carrier 5 in the opposite direction to FIG. 5. Two respective information carrier protrusions 19 are arranged on the back of each arm portion 18. These are approximately wedge-shaped and prepared to engage in corresponding counter geometries in the corner bulges 12 of the container tray 2.

Figure 7:
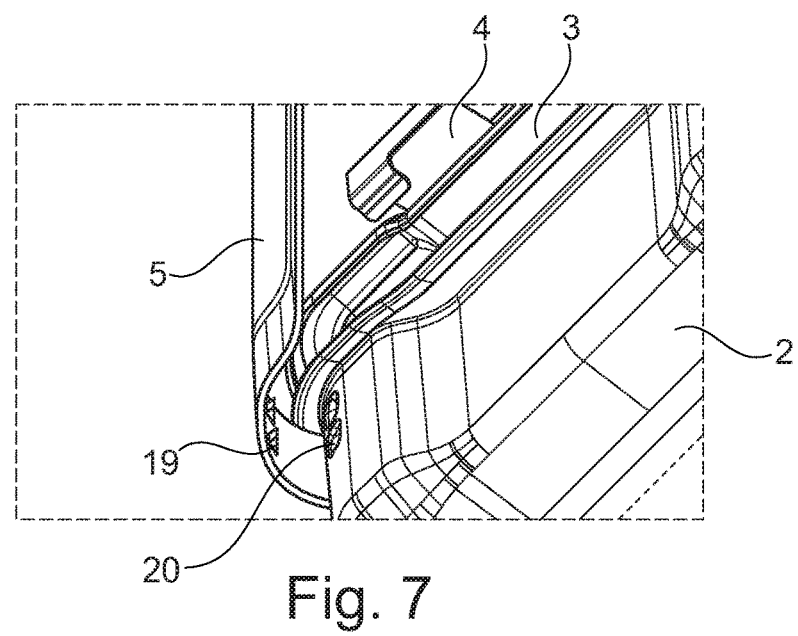
FIG. 7 is a partial perspective view showing the closure element before it comes into contact with the container tray.
Figure 8:
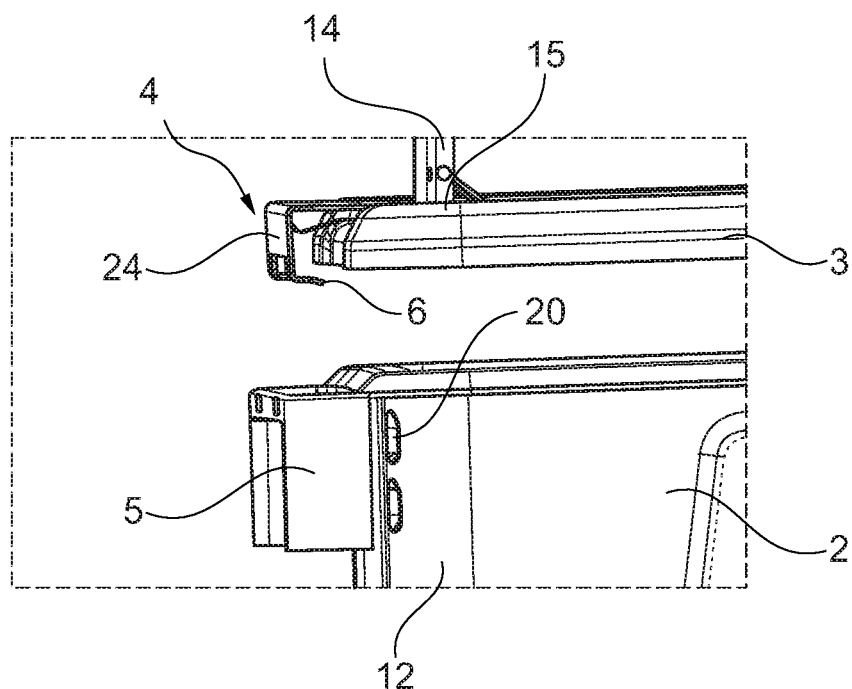
FIG. 8 is a partial perspective view showing the sterile container unit in a first operating state.

The counter geometries are shown in FIG. 7. They are referenced as a container notch 20. This serves to define the position of the information carrier 5 on the side wall of the container tray 2 in a form-fit manner. The other components shown in FIG. 7 have already been explained in connection with FIGS. 1 to 6, therefore they will not be described here.

FIGS. 8 to 11 show how the container lid 3 is placed on the container tray 2 by fixing/clamping the information carrier 5 by pivoting the closure element 4. In the state shown in FIG. 8, the locking lever 14 of the closure element 4 is actuated so that the clamp portion 24 protrudes. Furthermore, the information carrier 5 is not yet in contact with the container tray 2.

Figure 9:
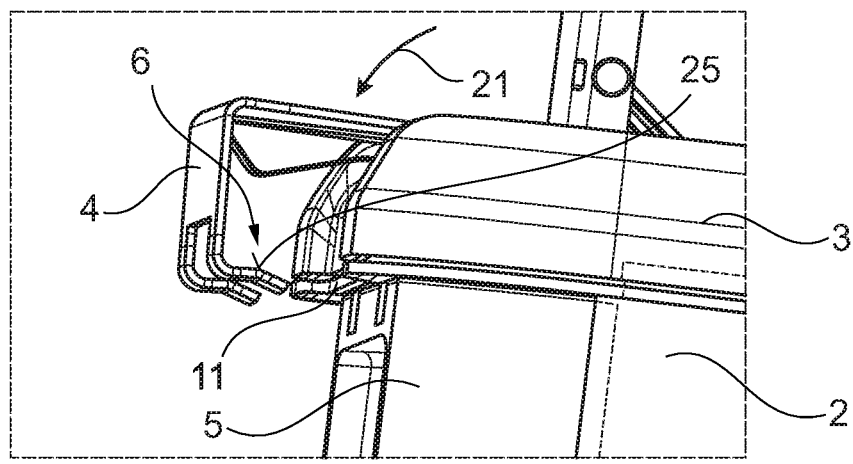
FIG. 9 is a partial perspective view showing the sterile container unit in a second operating state.

The first step for closing the container is shown in FIG. 9: the information carrier 5 is attached/in close contact with the container tray 2. Thus, the information carrier protrusions 19 engage in the container notches 20 (not visible). Furthermore, the container lid 3 is placed on the container tray 2 without pivoting movement of the closure element 4. The locking latch protrusions 6 have an attachment point or line or surface 25 in their form of a tongue, which is intended to initiate the pre-tensioning force against the clamping lug 7.

Figure 10:
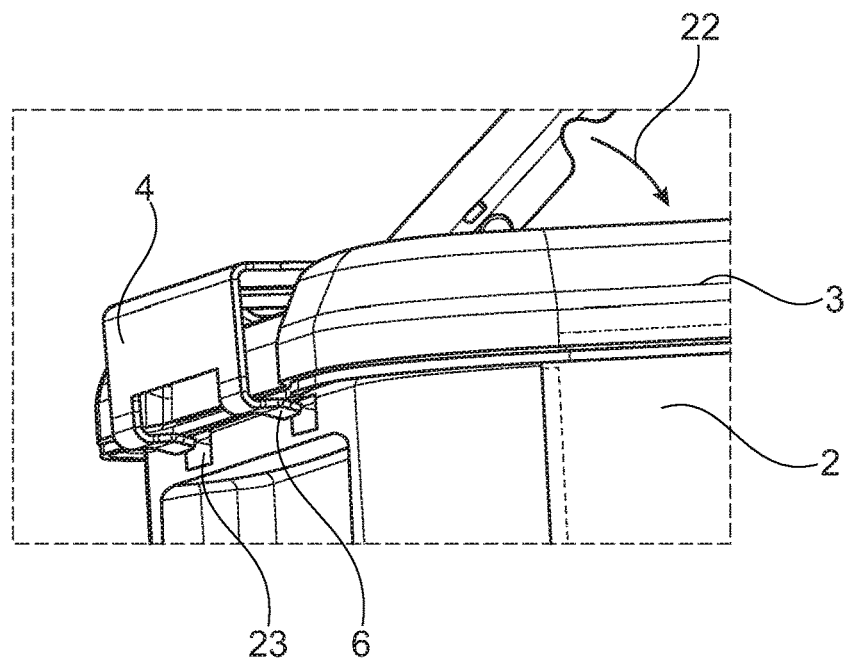
FIG. 10 is a partial perspective view showing the sterile container unit in a third operating state.
Figure 11:
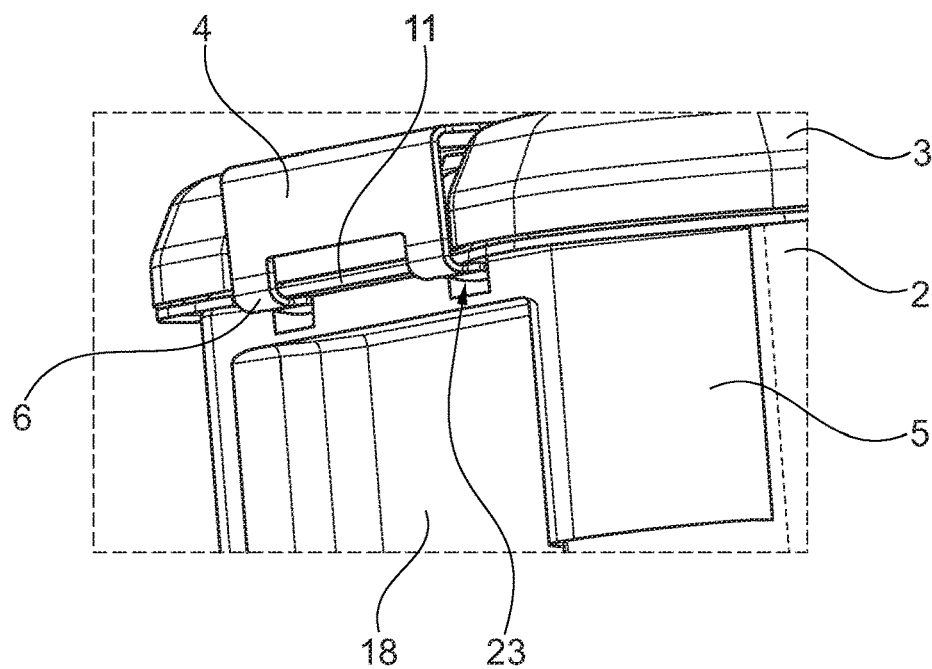
FIG. 11 is a partial perspective view showing the sterile container unit in a fourth operating state.

A first pivoting movement 21 to be performed for closing is indicated in FIG. 9. The resulting state is shown in FIG. 10. The locking latch protrusions 6 of the closure element 4 are already close to the engagement pockets 23 formed by the information carrier 5. The respective attachment points 25 of the clamp portion 24 are prepared to form a contact with the corresponding counter surfaces of the engagement pockets 23.

For final closing, a second pivoting movement 22 (see FIG. 10) is to be carried out, so that the sterile sealed state (see FIG. 11) is achieved. In this state, the locking latch protrusions 6 engage in the engagement pockets 23 in such a clamping manner that the information carrier 5 is fixed to the remaining sterile container unit 1. In order to release the information carrier 5, the locking lever 14 simply has to be pivoted in the opposite direction to arrows 21 and 22.

The invention claimed is:

1. A sterile container unit for receiving sterilized items or items to be sterilized, the sterile container unit comprising:
 a container tray;
 a container lid configured to be coupled in a sealing manner with the container tray via a closure element; and
 an information carrier configured to be fastened to the container tray to provide information about contents of the sterile container unit,
 the container tray, the closure element, and the information carrier being matched to each other in such a way that the information carrier is secured to the container tray by the closure element by actuation of the closure element for a sealing coupling of the container lid to the container tray, wherein the closure element forms at least one locking latch protrusion which is configured to engage in an engagement pocket formed by/on the information carrier upon reaching a sealing closure position,
 the closure element being designed in the form of a pawl, a locking bracket, or a latch, which is held displaceably on upper and outer sides of the container lid, and projects beyond an outer edge of the container lid and configured to be manually displaced or pivoted in a first direction towards the outer edge and a second direction away from the outer edge,
 the container tray comprising a tray circumference and forms, at least within an area of the closure element as well as on the tray circumference, a container collar or edge which, during a movement of the closure element towards the outer edge, is gripped underneath by the outer edge and thereby pull the container lid against the tray circumference in order to thus close an interior of the sterile container unit in a sealing manner,
 the information carrier being loosely held on a side surface of the container tray within an effective range of the closure element and is pressed against the container tray and thereby secured only by the closure element itself during its movement in the first direction towards the outer edge, and
 the information carrier having a plurality of information carrier projections on a rear side of the information carrier facing the container tray and a corresponding number of container notches formed on the side surface of the container tray, and the information carrier projections engage in said corresponding number of container notches in a form-fitting manner for loosely holding the information carrier on the container tray.

2. The sterile container unit according to claim 1, wherein the at least one locking latch protrusion, forming an attachment point, is or has a curved spring tongue which, in pressure contact with the engagement pocket, causes the at least one locking latch protrusion to be spring pre-tensioned in such a way that it clamps the information carrier between itself and the container tray while also pulling the container lid against the container tray.

3. The sterile container unit according to claim 1, wherein the container tray has a side surface, said side surface having a container collar protruding from the side surface in such a way that the container collar forms a contact edge/shoulder for the information carrier extending at least in sections complementary to the side surface.

4. The sterile container unit according to claim 3, wherein the information carrier forms a contact shoulder which is prepared to be/come into flat contact with the container collar at least in sections.

5. The sterile container unit according to claim 3, wherein the closure element has a clamp portion enclosing the container lid and the container collar, from which the at least one locking latch protrusion extends substantially parallel to an upper side of the container lid to at least partially engage under the container collar while clamping the information carrier.

6. The sterile container unit according to claim 1, wherein after/with a reverse actuation of the closure element in an opening direction, the information carrier is unlocked and thus a reversible release of the information carrier from the container tray is enabled.

7. The sterile container unit according to claim 1, wherein the container lid forms/has a primary seal and a secondary seal which are configured for contact with the container tray and thus create a sterile barrier between the sterile container unit and the environment.

8. The sterile container unit according to claim 1, wherein the closure element has a locking lever, the pivoting of which rigidly couples the information carrier to the container tray and the container lid.

9. The sterile container unit according to claim 1, wherein the information carrier projections are wedge-shaped.

10. A sterile container unit for receiving sterilized items or items to be sterilized, the sterile container unit comprising:
- a container tray;
- a container lid configured to be coupled in a sealing manner with the container tray via a closure element; and
- an information carrier configured to be fastened to the container tray to provide information about contents of the sterile container unit,
- the container tray, the closure element, and the information carrier being matched to each other in such a way that the information carrier is secured to the container tray by the closure element by actuation of the closure element for a sealing coupling of the container lid to the container tray,
- the container tray having a side surface, said side surface having a container collar protruding from the side surface in such a way that the container collar forms a contact edge/shoulder for the information carrier extending at least in sections complementary to the side surface,
- the side surface of the container tray having a corner bulge at its respective transitions to adjacent side surfaces of the container tray, wherein in said corner bulge at least one hollow-like container notch is formed, which is configured to form-fittingly receive a projection formed/arranged on the information carrier.

11. A sterile container unit for receiving sterilized items or items to be sterilized, the sterile container unit comprising:
- a container tray;
- a container lid configured to be coupled in a sealing manner with the container tray via a closure element; and
- an information carrier configured to be fastened to the container tray to provide information about contents of the sterile container unit,
- the container tray, the closure element, and the information carrier being matched to each other in such a way that the information carrier is secured to the container tray by the closure element by actuation of the closure element for a sealing coupling of the container lid to the container tray,
- the information carrier having a plurality of information carrier projections on its rear side facing the container tray and a corresponding number of container notches formed on the side surface of the container tray, and the information carrier projections engage in said corresponding number of container notches in a form-fitting manner for loosely holding the information carrier on the container tray.

12. The sterile container unit according to claim 11, wherein the information carrier projections are wedge-shaped.

* * * * *